United States Patent [19]

Drake

[11] 4,288,626
[45] Sep. 8, 1981

[54] PROCESS FOR HYDROGENATION OF UNSATURATED DINITRILES

[75] Inventor: Charles A. Drake, Bartlesville, Okla.

[73] Assignee: Phillips Petroleum Company, Bartlesville, Okla.

[21] Appl. No.: 184,520

[22] Filed: Sep. 5, 1980

[51] Int. Cl.$^3$ .................... C07C 85/12; C07C 85/26; C07C 121/20; C07C 121/28
[52] U.S. Cl. ............................. 564/491; 260/465 H; 260/465.8 R; 564/373; 564/375; 564/448; 564/492; 564/493
[58] Field of Search ................... 564/491, 345, 493; 260/465.8 R

[56] References Cited

U.S. PATENT DOCUMENTS

| | | | |
|---|---|---|---|
| 3,490,865 | 1/1970 | Huxley | 23/3 |
| 3,840,583 | 10/1974 | Turk et al. | 260/465.8 R |
| 3,880,929 | 4/1975 | Drake | 564/491 |
| 3,962,337 | 6/1976 | Drake | 564/493 |
| 4,235,808 | 11/1980 | Drake | 260/465.8 R |

OTHER PUBLICATIONS

Hersh, "Molecular Sieves", pp. 78–83, (1962).

*Primary Examiner*—John Doll

[57] ABSTRACT

A process for prolonging the activity of catalysts during the hydrogenation of unsaturated dinitriles comprising pretreating the dinitrile feed with a crystalline zeolite.

9 Claims, No Drawings

PROCESS FOR HYDROGENATION OF UNSATURATED DINITRILES

This invention relates to a process for the preparation of saturated diamines or saturated dinitriles by the catalytic hydrogenation of unsaturated aliphatic dinitriles.

Various processes for the catalytic hydrogenation of unsaturated dinitriles to saturated diamines are known in the art. Examples of such processes are disclosed in U.S. Pat. Nos. 3,880,929 and 3,962,337, the disclosures of which are incorporated herein by reference.

One technique of preparing a feedstock of unsaturated aliphatic dinitrile for use in such hydrogenations is disclosed in U.S. Pat. No. 3,840,583, the disclosure of which is also incorporated herein by reference. That process generally involves reacting at least one olefinic hydrocarbon reactant, at least one olefinically unsaturated mononitrile reactant and at least one monoadduct reaction product of an olefinic hydrocarbon compound and an olefinically unsaturated mononitrile compound to form a reaction product containing at least one olefinically unsaturated dinitrile.

The present invention is based upon the discovery that when hydrogenation reactions are performed upon the reaction product of processes of the type disclosed in U.S. Pat. No. 3,840,583, the activity of the hydrogenation catalyst can be greatly improved by first contacting the reaction product with a crystalline zeolite. For commercial use, a long catalyst life is, of course, desirable so that less frequent changes of catalyst are required and so that a product with lower average levels of unsaturation can be obtained.

The feedstock that is subjected to hydrogenation in accordance with the present invention is the reaction product obtained by reacting reactants consisting essentially of at least one olefinic hydrocarbon reactant, at least one olefinically unsaturated mononitrile reactant and at least one monoadduct reaction product of an olefinic hydrocarbon compound and an olefinically unsaturated mononitrile compound.

The olefinically unsaturated mononitrile compounds can be the same or different and are selected from those containing a cyano group attached to a carbon atom adjacent and doubly bonded to a carbon atom which is attached to at least one hydrogen atom. Such reactants and compounds include those of the formula

RCH=CR—CN wherein each R can be the same or different and is independently selected from the group consisting of hydrogen, alkyl, cycloalkyl, and aryl hydrocarbyl radicals or combinations thereof. Preferably, the total number of carbon atoms is within the range of 3 to 10, more preferably from 3 to 6. Examples of such unsaturated mononitrile compounds are acrylonitrile, metha acrylonitrile, 2-butenenitrile, 2-hexenenitrile, 2-decenenitrile, 5-methyl-2-hexenenitrile, 4-methyl-2-heptenenitrile, 3-cyclohexyl-2-propenenitrile, 4-phenyl-2-butenenitrile, 3(p-tolyl)-2-propenenitrile, and the like.

The olefinic hydrocarbon reactants and olefinic hydrocarbon compounds used to make the monoadduct can be the same or different and are selected from those containing at least one olefinic linkage having joined thereto a carbon atom having at least one hydrogen atom attached thereto. Such reactants and compounds thus include those olefins having within their molecule the functionality

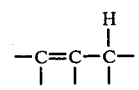

Specific examples of olefins that can be employed in the process of this invention include hydrocarbons such as propylene, isobutylene, 2-butene, 1-pentene, 1,5-hexadiene, cyclohexene, 1,5-cyclooctadiene, 2,4,4-trimethyl-1-pentene, alpha-methylstyrene, beta-methylstyrene, allylcyclohexene, allylbenzene, 1-decene, 1-dodecene; esters such as ethyl 5-methyl-5-hexenoate; alcohols such as methallyl alcohol; and aldehydes such as 5-methyl-5-hexenal, and the like. Preferred olefin reactants contain from 3 to 12 carbon atoms with from 1 to 2 ethylenically unsaturated, nonconjugated double bonds as the sole aliphatic unsaturation. Even more preferred olefin reactants are open chain monoolefinic hydrocarbons. Especially preferred are monoolefinic hydrocarbon reactants having from 3 to 12 carbon atoms and having an alkyl group, preferably methyl, as a side chain attached to at least one of the carbon atoms comprising the ethylenic linkage.

The monoadduct can be prepared separately or if desired during the diadduct formation by the continuous or intermittent addition of amounts of the olefin and unsaturated mononitrile compounds that are substantially equivalent to the amount of monoadduct reaction product consumed to diadduct.

Any suitable reaction conditions can be used for forming the monoadduct and diadduct.

Any suitable amount of olefin, unsaturated mononitrile and monoadduct reaction product can be employed in preparing the diadduct. In general, a suitable mol ratio of monoadduct reaction product to olefin varies within the range of from about 5:1 to about 0.2:1, and preferably varies from about 2:1 to about 0.5:1. In general, a suitable mol ratio of monoadduct reaction product to unsaturated mononitrile varies within the range of from about 10:1 to about 0.2:1, and preferably varies from about 5:1 to about 0.8:1.

The reaction time employed in producing the diadduct can vary widely. Generally a time period of from about a few minutes to about 48 hours and more preferably from about 1 hour to about 5 hours is an adequate period of time for olefin, unsaturated mononitrile and a monoadduct reaction product to be suitably admixed in the preparation of reaction products in high yields.

The reaction temperatures that can be employed in forming the diadduct can vary widely. Generally, however, suitable reaction temperatures are within the range of from about 100° C. to about 500° C., and preferred are within the range of from about 240° C. to about 350° C.

The reaction pressures suited to the diadduct formation also vary widely. Reaction pressures within a range of from about 0 atmospheres pressure to about 100,000 psig can be employed; however, reaction pressures within the range of from about 500 psig to about 4,000 psig are preferably employed.

The diadduct formation can be carried out in the presence of or the absence of a polymerization inhibitor. The presence of a polymerization inhibitor often advantageously limits or restricts side reactions within the reaction media such as the dimerization or polymerization of an unsaturated nitrile reactant. Accordingly, in a preferred embodiment a polymerization inhibitor is employed. Generally, the inhibitor can be employed in amounts of from about 0.001 to about 5, preferably from about 0.1 to about 1 percent by weight, based on the unsaturated mononitrile reactant. Suitable inhibitors include hydroquinone, 2,6-di-tertiarybutyl-paracresol, 2,6-di-tertiarybutyl hydroquinone, 4-tertiarybutyl catechol, para-hydroxydiphenylamine, and the like, and combinations thereof.

The diadduct formation is preferably carried out in the presence of a solvent or a diluent which is nonreactive with either the reactants or the reaction products. Representative of commercially available nonreactive solvents that can be employed are the following: benzene, toluene, para xylene, ortho xylene, meta xylene, ethylbenzene, diethyl ether, ethylpropyl ether, dibutyl ether, tetrahydrofuran, dioxane, cyclohexane, carbon tetrachloride, methylene chloride, and the like and mixtures thereof.

An exemplary diadduct reaction product resulting from the reaction of isobutylene, acrylonitrile, and the monoadduct of isobutylene and acrylonitrile is a composition consisting essentially of a mixture consisting of the major isomer species 5-methylenenonanedinitrile and 5-methyl-4-nonenedinitrile, that contains minor isomer species 2-methyl-4-methyleneoctanedinitrile, 2,4-dimethyl-4-octenedinitrile, 2,4-dimethyl-3-octenedinitrile, 2,6-dimethyl-4-methyleneheptanedinitrile and 2,4,6-trimethyl-3-heptenedinitrile.

The present invention is considered to be applicable to generally any of the hydrogenation processes used for the conversion of unsaturated dinitriles to saturated dinitriles or saturated diamines. Suitable catalysts for the hydrogenation thus can include those based on palladium or ruthenium. For example, the catalysts can be elemental ruthenium, elemental palladium, or compounds of ruthenium or palladium which are reducible by hydrogen under suitable hydrogenation conditions to finely divided elemental ruthenium or palladium. Examples of such suitable hydrogen-reducible compounds include oxides, halides, nitrates, oxalates, acetates, carbamates, propionates, tartrates, hydroxides, and the like and mixtures of two or more thereof. Specific examples include elemental ruthenium, ruthenium oxide, ruthenium chloride, ruthenium nitrate, ruthenium acetate, ruthenium carbonate, ruthenium hydroxide, elemental palladium, palladium oxide, palladium chloride, palladium nitrate, palladium oxalate, palladium acetate and palladium hydroxide, and the like.

In the practice of the present invention the palladium catalysts are generally used for the hydrogenation of the olefinic unsaturation of unsaturated dinitriles to give saturated dinitriles. The ruthenium catalysts are generally used for the reduction of the unsaturated and/or saturated dinitriles to saturated diamines.

It is preferable in the practice of the present invention to employ catalytic amounts of elemental ruthenium or elemental palladium on a solid catalyst carrier which does not deleteriously affect the catalytic hydrogenation process of the invention. Such supports include, for example, carbon, kielselguhr, silica, alumina, silica-alumina, calcium carbonate, asbestos, pumice, clays, and the like, and mixtures of two or more thereof. The ruthenium or palladium can be added to the catalyst support by any of the methods well known in the art. For example, the supported catalyst can be prepared by dry mixing the components or by impregnating the support with a solution or dispersion of ruthenium or palladium in elemental form or in the form of reducible compounds thereof. The supported catalysts can be pretreated with hydrogen to reduce the palladium or ruthenium compounds, or such reduction can be achieved in the hydrogenation reactor. When a support is employed, the amount of elemental ruthenium or palladium on the support material will generally be in the range of about 0.05 to about 20 weight percent, and preferably in the range of about 0.1 to about 10 weight percent based on the weight of the total catalyst components. Examples of suitable catalysts include ruthenium or palladium on alumina, each having a catalytic metal content of about 5 weight percent based on the total weight of the catalyst and support material. Other suitable catalysts include palladium on charcoal (10 weight percent palladium), ruthenium dioxide, and ruthenium on charcoal (5 weight percent ruthenium). The specifically named catalysts are commercially available catalytic materials.

The amount of catalyst employed in a batch hydrogenation process of the present invention can be expressed in terms of the weight percent of catalytic metal based on the weight of compound being hydrogenated. The amount of catalytic metal can be any suitable quantity, but generally will be in the range of about 0.01 to about 20, and preferably in the range of about 0.05 to about 5, weight percent of palladium or ruthenium based on the hydrogenation substrate. The amount of catalyst used for a continuous hydrogenation process in accordance with the present invention can be any suitable quantity, but generally is such that a liquid hourly space velocity (LHSV) in the range of about 0.01 to about 10, and preferably in the range from about 0.05 to about 5, volumes of unsaturated dinitrile plus diluent per volume of catalyst will be attained.

The hydrogen pressure utilized in the hydrogenation process in accordance with the present invention can be any suitable pressure but is generally within the range of about 500 to about 5000 psig (3.5 to 35 MPa) and preferably in the range of about 1000 to 3000 psig (6.9 to 20.7 MPa). The temperature utilized under the hydrogenation conditions of the present invention using palladium catalysts can be of any suitable value, but is generally in the range of about 20 to about 250° C. and preferably in the range of about 80 to about 170° C. The temperature utilized under the hydrogenation conditions of the present invention when using ruthenium catalysts can be of any value, but is generally in the range from about 80 to about 250° C. and preferably in the range from about 125 to about 170° C. Any suitable time period can be employed in the hydrogenation process in accordance with the present invention, but will generally be in the range of about 15 minutes to about 5 hours for a batch process.

Any suitable diluent can be employed in the hydrogenation process of the present invention when palladium is used as a catalyst, but generally the diluent will be selected from the group consisting of alcohols having 1 to 12 carbon atoms per molecule, unsubstituted acyclic or unsubstituted cyclic ethers having from 4 to 12 carbon atoms per molecule, and mixtures of two or more thereof. The presently preferred diluent when palladium is used as a catalyst is methanol.

Any suitable diluent can be employed in the hydrogenation process of the present invention when ruthenium is used as a catalyst, but generally the diluent will be selected from the group consisting of alcohols having 2 to 12 carbon atoms per molecule, unsubstituted acyclic or unsubstituted cyclic ethers having 4 to 12 carbon atoms per molecule, and mixtures of two or more thereof. Currently preferred diluents for use with ruthenium catalysts are tertiary alcohols, the more preferred diluent being tertiary-butyl alcohol.

Any suitable suppressant can be employed to suppress undesirable side reactions in the hydrogenation of unsaturated dinitriles, but generally ammonia is employed in the hydrogenation of unsaturated dinitriles with ruthenium catalysts as a means of suppressing undesirable side reactions such as the formation of secondary and tertiary amines. In general, the mol ratio of ammonia to cyano groups, there being two cyano groups per unsaturated dinitrile molecule, will be in the range of about 1:1 to about 25:1 and preferably in the range of about 7:1 to about 15:1.

Recovery of the desired end product, the saturated diamines or dinitriles, as well as any resulting reaction by-products, any unconsumed reactants, ammonia, hydrogen, and/or diluents, can be carried out by any conventional separation means. In general, at the conclusion of the catalytic hydrogenation process, the reaction zone effluent is cooled and depressurized with the recovery, if desired, of any ammonia or diluent which is vented from the reaction zone effluent during the depressurization operation. The ammonia or diluent can be returned or recycled to the hydrogenation zone if desired. The reaction products can be separated from the catalyst by conventional filtration means. The filtrate containing the hydrogenation product can be conveniently separated from any reaction byproducts or any diluent remaining in the filtrate by any conventional fractional distillation.

In accordance with the present invention, the reaction product mixture from the diadduct formation is treated with a crystalline zeolite prior to being subjected to the hydrogenation. Crystalline zeolites are well known forms of aluminosilicates having various amounts of water of hydration associated therewith. Both natural and synthetic crystalline zeolites are considered useful. Examples of typical natural zeolites include chabazite, erionite, faujasite, mordenite, sodalite, phacolite, gmelinite, harmotone, and the like. Examples of synthetic crystalline zeolites include those zeolites designated by the Linde Division of Union Carbide Corporation by the letters X, Y, A, and L (these zeolites are described in U.S. Pat. Nos. 2,882,244; 3,130,007; 2,882,243; and Belgium Pat. No. 575,117, respectively). A particularly preferred zeolite is a calcium exchanged zeolite sold by Union Carbide as Linde AW-500.

Generally prior to use it is desirable to assure that the zeolites are substantially dry. This can be achieved by heating the zeolite in a ventilated oven at a temperature in the range of about 130° C. to about 140° C. for several hours, typical around 3 hours.

The diadduct reaction product mixture can be brought into contact with the zeolite material in any suitable form, but generally in the form of undiluted liquid, or in one or more diluents such as hydrocarbons, alcohols, cyclic ethers, acyclic ethers, or the like. Generally, the technique simply involves passing the mixture through a column of the zeolite. It is often desirable to use an inert gas to help drive the mixture through the zeolite. The optimum amount of contact between the zeolite and the feedstock can be readily determined by routine experimentation.

Temperatures used during the purification of the diadduct reaction product mixture can be any suitable purification temperature, but generally will be in the range of about −10° to about 150° C., and preferably in the range of about 0° to about 75° C. The pressure of the inert gas can be any suitable purification pressure, but will generally be in the range of about 0.01 to about 100 atmospheres (0.001 to 10.1 MPa), and preferably in the range from about 0.1 to about 5 atmospheres (0.01 to 0.51 MPa). Flow rates through a column will generally be in the range of about 0.01 to about 50 mL of diadduct reaction product mixture per mL of zeolite per hour, preferably about 0.1 to about 5.

A further understanding of the invention and its advantages will be provided by the following example in which various materials are used to pretreat the feedstock which is the product resulting when isobutylene, acrylonitrile and the monoadduct of isobutylene and acrylonitrile are reacted to produce 5-methyl-4-nonenedinitrile. The reaction product contains 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile.

EXAMPLE I

Separate portions of the diadduct reaction product were subjected to hydrogenation to evaluate the effect of pretreatments. The hydrogenation catalyst was ruthenium on gamma-alumina (about 0.5 weight percent ruthenium based on the weight of the total catalyst components). Each run was carried out in a 0.5 inch diameter × 20 inch length laboratory continuous reactor which was charged with 20 grams of the catalyst. The reactor was flushed with nitrogen and the catalyst activated at 150° C., 1500 psig (10.3 MPa), and a 1 liter per minute hydrogen flow.

In each of the runs, a solution composed of 9 weight percent pretreated diadduct feedstock, 9 weight percent ammonia, and 82 weight percent tertiary butyl alcohol was fed at a liquid hourly space velocity of about 2 volumes of solution per volume of catalyst. The reaction conditions during the hydrogenations were 1500 psig pressure (10.3 MPa), 140° C., and 1 liter per minute hydrogen flow. Samples were collected at regular time intervals and analyzed by gas-liquid chromatography after evaporating the ammonia and the tertiary-butyl alcohol diluent.

In Run No. 1, the solution of diadduct reaction product was not given any pretreatment. The other runs employed various treating agents to pretreat the diadduct reaction product. The pretreatments involved passing the diadduct reaction product through a 20 inch × 1 inch diameter column filled with the treating agent at a rate of about 2 mL per mL per hour of treating agent. Each treating agent was dried prior to use for about 3 hours at a temperature in the range of about 130° C. to about 140° C. The treating agents and their relative effects are summarized in the following table.

TABLE

| Run No. | Pretreatment | Saturated Diamine in Product, Wt. % | |
|---|---|---|---|
| | | After 4 Hours | After 19 Hours |
| 1 | None | 64 | 51 |
| 2 | MgO (30–60 mesh) | 69 | 55 |

TABLE-continued

| Run No. | Pretreatment | Saturated Diamine in Product, Wt. % After 4 Hours | After 19 Hours |
|---|---|---|---|
| 3 | Silica-alumina[a] | 77 | 25 |
| 4 | 13X Zeolite[b] | 71 | 61 |
| 5 | 4A Zeolite[c] | 79 | 66 |
| 6 | 3A Zeolite[d] | 82 | 67 |
| 7 | 5A Zeolite[e] | 100 | 96 |

[a] A silica-alumina cogel ($SiO_2$ - 64.6%, $Al_2O_3$ - 33.6%, $Na_2O$ - 0.15%, $Fe_2O_3$ - 0.18%, CaO - 0.03%). The cogel was in the form of 1/16 inch extrudate.
[b] $Na_{86}[(AlO_2)_{86}(SiO_2)_{106}]$ in the form of 1/16 inch extrudate.
[c] $Na_{12}[(AlO_2)_{12}(SiO_2)_{12}]$ in the form of 1/16 inch extrudate.
[d] $K_9Na_3[(AlO_2)_{12}(SiO_2)_{12}]$ in the form of 1/16 inch extrudate.
[e] $Ca_6[(AlO_2)_{12}(SiO_2)_{12}]$ in the form of 1/16 inch extrudate.

The data shown in the Table clearly indicate that the activity of the hydrogenation catalyst remains better longer when the diadduct reaction product mixture is pretreated with zeolites than with other materials such as magnesia or silica-alumina cogel. Especially good results are obtained using the 5A zeolite, sold in commerce as Linde AW-500, see Run 7.

Reasonable variations and modifications to the invention are possible within the scope of the foregoing disclosure and the appended claims.

What is claimed is:

1. In a process for producing saturated diamines or dinitriles from an olefinically unsaturated dinitrile feedstock comprising the reaction product obtained by contacting under suitable reaction conditions for producing said unsaturated dinitrile reactants consisting essentially of at least one olefinically unsaturated mononitrile reactant and at least one monoadduct reaction product of an olefinic hydrocarbon compound and an olefinically unsaturated mononitrile compound wherein each said olefinically unsaturated mononitrile reactant and each said olefinically unsaturated mononitrile compound contain a cyano group attached to a carbon atom adjacent and doubly bonded to a carbon atoms which is attached to at least one hydrogen atom and each said olefinic hydrocarbon reactant and each said olefinic hydrocarbon compound have at least one olefinic linkage having joined thereto a carbon atom having at least one hydrogen atom attached thereto comprising subjecting the feedstock to suitable hydrogenation conditions in the presence of hydrogen and a suitable hydrogenation catalyst, the improvement comprising contacting the feedstock with a crystalline zeolite so as to extend the activity of said hydrogenation catalyst.

2. A process according to claim 1 wherein said olefinically unsaturated dinitrile feedstock consists essentially of the reaction product obtained when isobutylene, acrylonitrile, and the monoadduct of isobutylene and acrylonitrile are reacted to produce 5-methyl-4-nonenedinitrile.

3. A process according to claim 2 wherein said zeolite is selected from X and A type zeolites.

4. A process according to claim 3 wherein said zeolite is a 5A zeolite having the formula $Ca_6[(AlO_2)_{12}(SiO_2)_{12}]$.

5. A process according to claim 2 wherein said hydrogenation catalyst comprises at least one of palladium or ruthenium.

6. A process according to claim 5 wherein said hydrogenation catalyst comprises ruthenium.

7. A process according to claim 6 wherein said hydrogenation is carried out with said olefinically unsaturated dinitrile feedstock in solution in tertiary butyl alcohol diluent and ammonia.

8. A process according to claim 7 wherein said zeolite is selected from a 3A, 4A, 5A, or 13X type zeolite.

9. A process according to claim 8 wherein said zeolite is a 5A zeolite having the formula $Ca_6[(AlO_2)_{12}(SiO_2)_{12}]$.

* * * * *